(12) United States Patent
Rodriguez et al.

(10) Patent No.: US 9,023,641 B2
(45) Date of Patent: May 5, 2015

(54) MICROFLUIDIC DEVICE AND LEUCOCYTE ANTIGEN MEDIATED MICROFLUIDIC ASSAY

(75) Inventors: Rodolfo R. Rodriguez, Cary, NC (US); Douglas J. Darr, Timberlake, NC (US)

(73) Assignee: Advanced Animal Diagnostics, Durham, NC (US)

( * ) Notice: Subject to any disclaimer, the term of this patent is extended or adjusted under 35 U.S.C. 154(b) by 1191 days.

(21) Appl. No.: 11/568,832

(22) PCT Filed: May 13, 2005

(86) PCT No.: PCT/US2005/016974
§ 371 (c)(1),
(2), (4) Date: Sep. 20, 2007

(87) PCT Pub. No.: WO2006/085897
PCT Pub. Date: Aug. 17, 2006

(65) Prior Publication Data
US 2009/0011451 A1    Jan. 8, 2009

Related U.S. Application Data

(60) Provisional application No. 60/570,543, filed on May 13, 2004.

(51) Int. Cl.
| | |
|---|---|
| *C12M 1/34* | (2006.01) |
| *B01L 3/00* | (2006.01) |
| *G01N 15/06* | (2006.01) |
| *G01N 33/48* | (2006.01) |
| *G01N 33/49* | (2006.01) |
| *G01N 33/50* | (2006.01) |
| *G01N 33/569* | (2006.01) |
| *G01N 15/00* | (2006.01) |

(52) U.S. Cl.
CPC ....... *G01N 33/56972* (2013.01); *B01L 3/50273* (2013.01); *G01N 2015/008* (2013.01); *B01L 3/5027* (2013.01); *B01L 2300/0816* (2013.01); *B01L 2300/0867* (2013.01); *B01L 2400/0406* (2013.01); *G01N 2333/8107* (2013.01)

(58) Field of Classification Search
None
See application file for complete search history.

(56) References Cited

U.S. PATENT DOCUMENTS

| | | | |
|---|---|---|---|
| 3,963,580 A | 6/1976 | Vedamuthu | |
| 4,190,020 A | 2/1980 | Tamas et al. | |
| 4,385,590 A | 5/1983 | Mortensen | |
| 4,615,878 A * | 10/1986 | Kass | 435/34 |

(Continued)

FOREIGN PATENT DOCUMENTS

| | | |
|---|---|---|
| WO | WO 94/10576 A1 | 5/1994 |
| WO | WO 01/70938 A1 | 9/2001 |

OTHER PUBLICATIONS

Cianciolo et al., Covalent complexes of antigen and alpha-macroglobulin: evidence for dramatically-increased immunogenicity, Vaccine (2002) 20:554-62.*

(Continued)

*Primary Examiner* — Christine Foster
(74) *Attorney, Agent, or Firm* — Myers Bigel Sibley Sajovec, P.A.

(57) ABSTRACT

The present invention relates to an leucocyte antigen mediated microfluidic assay and a microfluidic device for analyzing a subjects' body fluids containing leucocytes to determine if the subject has been previously exposed to a predetermined antigen.

15 Claims, 2 Drawing Sheets

(56) References Cited

U.S. PATENT DOCUMENTS

| | | | |
|---|---|---|---|
| 4,756,884 A * | 7/1988 | Hillman et al. | 422/73 |
| 5,116,731 A | 5/1992 | Wilhelms | |
| 5,168,044 A | 12/1992 | Joyce et al. | |
| 5,302,903 A | 4/1994 | De Jong et al. | |
| 5,360,719 A * | 11/1994 | Levine et al. | 435/29 |
| 5,434,082 A | 7/1995 | Yamamoto et al. | |
| 5,480,778 A | 1/1996 | Levine et al. | |
| 5,550,148 A | 8/1996 | West et al. | |
| 5,628,964 A | 5/1997 | Tassitano | |
| 5,637,469 A | 6/1997 | Wilding et al. | |
| 5,660,993 A | 8/1997 | Cathey et al. | |
| 5,792,964 A | 8/1998 | van den Berg | |
| 5,807,684 A | 9/1998 | Simmons et al. | |
| 5,849,488 A | 12/1998 | Alatossava et al. | |
| 5,948,686 A | 9/1999 | Wardlaw | |
| 6,004,821 A | 12/1999 | Levine et al. | |
| 6,038,030 A | 3/2000 | van den Berg | |
| 6,073,580 A | 6/2000 | Graupner et al. | |
| 6,127,184 A | 10/2000 | Wardlaw | |
| 6,180,314 B1 | 1/2001 | Berndt | |
| 6,197,538 B1 | 3/2001 | van den Berg et al. | |
| 6,235,536 B1 | 5/2001 | Wardlaw | |
| 6,287,771 B1 | 9/2001 | Imamura et al. | |
| 6,297,045 B1 | 10/2001 | Takahashi et al. | |
| 6,307,362 B1 | 10/2001 | Mangan | |
| 6,330,350 B1 | 12/2001 | Ahn et al. | |
| 6,350,613 B1 * | 2/2002 | Wardlaw et al. | 436/10 |
| 6,479,017 B2 | 11/2002 | Miefalk | |
| 6,493,071 B2 | 12/2002 | van den Berg et al. | |
| 6,658,143 B2 | 12/2003 | Hansen et al. | |
| 6,723,290 B1 | 4/2004 | Wardlaw | |
| 2002/0028158 A1 | 3/2002 | Wardlaw | |
| 2002/0054831 A1 | 5/2002 | Berg et al. | |
| 2002/0055178 A1 | 5/2002 | Wardlaw | |
| 2002/0183600 A1 | 12/2002 | Tsenkova et al. | |
| 2002/0198441 A1 | 12/2002 | Tsenkova | |
| 2003/0143637 A1 * | 7/2003 | Selvan et al. | 435/7.9 |
| 2004/0019300 A1 | 1/2004 | Leonard | |

OTHER PUBLICATIONS

Ron L Bardell, Bernhard H Weigl, Natasa Kesler, Thomas Schulte, Jon Hayenga, Fred Battrell; Microfluidic Disposables for Cellular and Chemical Detection—CFD Model Results and Fluidic Verification Experiments.

Maurizio Provenzano, Simone Mocellin, Paola Bonginelli, Dirk Nagrosen, Seog-Woon Kwon and David Stroncek; Ex vivo screening for immunodominant viral epotopes by quantification real time polymerase chain reaction (qRT-PCR); Journal of Translational Medicine; Dec. 15, 2003; 1:12; Journal of Translational Medicine.

Perihan Nalbant, Louis Hodgson, Vadim Kraynov, Alexei Toutchkine, Klaus M. Hahn; Activation of Endogenous Cdc42 Visualized in Living Cells; Science; Sep. 10, 2004; 1615-1619; vol. 305; Science Magazine; Chapel Hill, NC.

Fatima, Fluorescence-Assisted Transmigration Invasion and Motility Assay; Tecan.

Taras A. Lyubchenko, Georjeana A. Wurth, and Adam Zweifach; Role of Calcium Influx in Cytotoxic T Lymphocyte Lytic Granule Exocytosis During Target Cell Killing; Immunity; Nov. 2001; vol. 15, 1-20; Cell Press; Denver, CO.

Kokura S, Wolf RE, Yoshikawa T, Granger DN, AW TY; T-lymphocyte-derived tumor necrosis factor exacerbates anoxia-reoxygenation-induced neutrophil-endothelial cell adhesion; Circ Rex.; Feb. 4, 2000; 86(2):205-13; PubMed.

Tilo Biedermann et al; Mast Cells Control Neutrophil Recruitment during T Cell-mediated Delayed-type Hypersensitivity Reactions through Tumor Necrosis Factor and Macrophage Inflammatory Protein 2; Journal of Experimental Medicine; Nov. 13, 2000; 1441-1452; vol. 192, No. 10; Rockefeller University Press.

S. J. Molesworth-Kenyon et al; A novel role for neutrophils as a source of T cell-recruiting chemokines IP-10 and Mig during the DTH response to HSV-1 antigen; J Virol. Aug. 2000;76(16):8050-7; Department of Microbiology and Immunology, University of South Alabama; Mobile, AL.

Shigeo Yamashiro et al; Phenotypic and functional change of cytokine-activated neutrophils: inflammatory neutrophils are heterogeneous and enhance adaptive immune responses; Journal of Leukocyte Biology; 2001;69:698-704; Society for Leukocyte Biology, Laboratory of Molecular Immunoregulation, National Cancer Institute at Frederick, Frederick, MD.

Tumpey, TM et al; Role for macrophage inflammatory protein 2(MIP-2), MIP-1alpha, and interleukin-1alpha in the delayed-type hypersensitivity response to viral antigen; PMID: 12134010 [PubMed—indexed for Medline]; Southeast Poultry Research Laboratory, U.S. Department of Agriculture, Agriculture Research Service, South Atlantic Area, Athens, GA.

Oleg Chertov et al; Identification of Human Neutrophil-derived Cathepsin G and Azurocidin/CAP37 as Chemoattractants for Mononuclear Cells and Neutrophils; J.Exp. Med.; Aug. 29, 1997; 739-747; vol. 186, No. 5; Frederick, MD.

Dennis D. Taub et al; T Lymphocyte Recruitment by Interleukin-8 (IL-8) IL-8-induced Degranulation of Neutrophils Releases Potent Chemoattractants for Human T Lymphocytes Both In Vitro and In Vivo; J. Clin. Invest.; Apr. 1996; 1931-1941; vol. 97, No. 8; Baltimore, MD.

Shigeo Yamashiro et al; Phenotypic and functional change of cytokine-activated neutrophils: inflammatory neutrophils are heterogenous and enhance adaptive immune responses; Journal of Leukocyte Biology; 2001;69:698-704; Society for Leukocyte Biology, Laboratory of Molecular Immunoregulation, National Cancer Institute at Frederick, Frederick, MD.

S. J. Molesworth-Kenyon et al; A novel role for neutrophils as a source of T cell-recruiting chemokines IP-10 and Mig during the DTH response to HSV-1 antigen; Journal of Leukocyte Biology; 2005;77:552-559; Society for Leukocyte Biology; Department of Microbiology and Immunology, University of South Alabama; Mobile, AL.

Fernandez-Segura E. et al; Shape, F-actin, and surface morphology changes during chemotactic peptide-induced polarity in human neutrophils; PMID: 7604967 [PubMed—indexed for Medline]; Anat Rec. Apr. 1995;241(4):519-28; Departmento de Biologia Celular e Histologia, Facultad de Medicina, Universidad de Granada, Spain.

Tvinnereim, AR et al; Neutrophil involvement in cross-priming CD8+ T cell responses to bacterial antigens; PMID: 15265934 [PubMed—indexed for Medline]; J. Immunol. Aug. 1, 2004;173(3):1994-2002; Department of Microbiology, University of Iowa, Iowa City, IA.

Nicholas S. Potter and Clifford V. Harding; Neutrophils Process Exogenous Bacteria Via an Alternate Class I MHC Processing Pathway for Presentation of Peptides to T Lymphocytes; Department of Pathology, Case Western Reserve University, Cleveland, OH.

Radsak M et al; Polymorphonuclear neutrophils as accessory cells for T-cell activation: major histocompatibility complex class II restricted antigen-dependent induction of T-cell proliferation; 1: Immunology. Dec. 2000;101(4):521-30; Institut for Immunologie and Medizinische Klinik der Universitat Heidelberg, Heidelberg, Germany.

Gavin P. Sandilands et al; Cross-linking of neutrophil CD11b results in rapid cell surface expression of molecules required for antigen presentation and T-cell activation; Immunology; vol. 114, Issue 3, p. 354—Mar. 2005; doi:10.1111/j.1365-2567.2004.02114.x.

Andrew JE Seely et al; Science review: Cell membrane expression (connectivity) regulates neutrophil delivery, function and clearance; Critical Care 2003; Jan. 9, 2003; 7:291-307; doi:10.1186/cc1853.

Larry A. Harshyne et al; Dendritic Cells Acquire Antigens from Live Cells for Cross-Presentation to CTL; The Journal of Immunology, 2001, 166:3717-3723; The American Association of Immunologists; University of Pittsburgh, PA.

Falk R.E. et al., "Antigen-Reactive Cells to Tumor Antigens in Normal and Tumor Patients", *Journal of Surgical Research*, vol. 20, No. 3, pp. 247-253, Mar. 1976.

Supplementary European Search Report Corresponding to European Application No. 05 85 6714; Date of Completion: Dec. 17, 2010, 3 Pages.

(56) References Cited

OTHER PUBLICATIONS

Dorland's Medical Dictionary, isolate, Copyright 2007, Jun. 16, 2010.
Ron L Bardell, Bernhard H Weigl, Natasa Kesler, Thomas Schulte, Jon Hayenga, Fred Battrell; Microfluidic Disposables for Cellular and Chemical Detection—CFD Model Results and Fluidic Verification Experiments, Proc. SPIE 4265, Biomedical Instrumentation Based on Micro- and Nanotechnology, 1 (May 21, 2001); doi:10.1117/12.427961, 13 pages total.
FATIMA, Fluorescence-Assisted Transmigration Invasion and Motility Assay; Tecan, (4 pages total).
Tumpey, TM et al; Role for macrophage inflammatory protein 2(MIP-2), MIP-1alpha, and interleukin-1alpha in the delayed-type hypersensitivity response to viral antigen; PMID: 12134010 [PubMed—indexed for Medline]; Southeast Poultry Research Laboratory, U.S. Department of Agricultuere Research Service, South Atlantic Area, Athens, GA, J Virol. Aug. 2002; 76(16):8050-7, Abstract Only.
Nicholas S. Potter and Clifford V. Harding; Neutrophils Process Exogenous Bacteria Via an Alternate Class I MHC Processing Pathway for Presentation of Peptides to T Lymphocytes; Department of Pathology, Case Western Reserve University, Cleveland, OH, J Immunol. Sep. 1, 2001;167(5):2538-46, title and portion of abstract only.

\* cited by examiner

MICROFLUIDIC DEVICE AND LEUCOCYTE ANTIGEN MEDIATED MICROFLUIDIC ASSAY

This application claims priority of provisional application Ser. No. 60/570,543 filed May 13, 2004.

BACKGROUND OF THE INVENTION

1. Field of the Invention

The present invention relates to an assay method and a microfluidic device for analyzing a subjects' body fluids containing leucocytes to determine if the subject has been previously exposed to the antigen. Specifically, the invention relates to an assay for observation, qualification and quantification of leucocyte measurement factors in a leucocyte containing fluid sample from a subject by exposure to a predetermined antigen in a novel microfluidic device in order to determine if there has been a prior exposure to the antigen.

2. Description of the Related Art

In leucocyte containing animals such as bird, mammals and especially humans, it is often necessary or determine if they have been previously exposed to a predetermined antigen. Antigens can be disease pathogens, allergy agents, toxins, infectious agents and the like. These days, because of the threat of bio-terrorism, not only are physicians concerned with normal exposure of their patients to various pathogens, the possibility of a civilian or military population being exposed to a terrorist act such as the anthrax events of late has created a need for tests which are simple, can be performed almost anywhere, are accurate and fast to determine if there has been a first prior exposure to a predetermined antigen in order to determine what if any method of treatment to use on the subject. In addition to the above, prior exposure to an antigen necessarily results after vaccination for infectious diseases. It is often desirable for a physician to determine that a vaccination has been successful in immunizing a subject or that after an extended time period that immunization from a subjects' prior vaccination remains above an acceptable level.

Antibodies are produced by certain lymphocytes, the B-lymphocytes, and are one of the body's defense mechanism against antigens in the blood stream and other body fluids containing leucocyte. The presence of circulating antibodies is an indicator that the subject is or has been actively fighting against such infectious agents as viral or bacterial antigens. A plethora of tests have been developed to directly and indirectly measure circulating antibodies from an ex vivo blood sample. More common methods include latex agglutination, enzyme linked immuno substrate assay, radioimmunoassay, radio immuno sorbent assay, indirect immuno fluorescence and the like. These antibody assays primarily rely on the production of antibody by B-lymphocytes and the measurement of their presence in sufficient quantities in the blood sample.

Serious problems exit however with antibody assays in this type of clinical testing. Firstly, not all disease states, toxins or maladies produce a significant enough antibody response from B-lymphocytes to be useful in antibody assays. A second problem with antibody tests arises when the time for production of antibodies, regardless of the quantity of antibodies produced, is sufficiently long such that by the time a diagnosis is made the patient may have suffered irreparable harm. In some cases several days may need to elapse before measurable quantities of antibodies are present in the blood. In antigen exposure situations where a subjects' medical treatment relies on a quick diagnosis, such low volume or long development time assays are essentially useless. Besides these problems, antibody assays often require highly skilled technicians to perform them and they may need to be performed in a laboratory setting. Not only does that mean the tests are costly, but it means that testing cannot be done on the site of an incident such as a terrorist attack, in the field or a doctors office, since samples must be sent back to the lab.

An alternative to antibody testing is the testing of T-lymphocytes especially memory T-lymphocytes, to determine if there has been a prior exposure to an antigen. T-lymphocytes are known to quickly undergo changes upon second antigen challenge. These changes are collectively referred to as measurement factors. Current lymphocyte testing relies on measurements of morphological factors and/or biochemical factors as an indication of activation by an antigen. Some of the known factors are listed in U.S. Pat. No. 5,480,778. These types of tests also have several difficulties. For example, some require use of radioactive isotopes, samples need to be centrifuged, the time to accomplish the tests can be extremely long (from half a day to several days in length), they require trained personnel to do the test in a lab, require several milliliters of blood, are designed to be used in assays where there is no fluid flow, where samples need to be diluted and the like. Further, the majority of the tests methods do not have the ability to accommodate more than a single mode i.e. a single measurement factor, of analysis. A further problem has been that histochemical staining and cellular morphology are not capable of being done together with most methods. Yet another problem with antibody assays are that T-lymphocytes represent a relatively small portion of leucocytes and even less a percentage of whole undiluted blood making observing or measuring them with small fluid samples extremely difficult.

One method is described in the art that is capable of looking at whole blood and separating it into different cell types. In U.S. Pat. No. 6,350,613 a method of admixing fluorescent dyes with a blood sample is described and target cells can be enumerated by means of a scanning instrument which is able to measure different wavelength of color signals emitted from the target cells in the sample and differentiate target cells from one another by reason of the emitted color signals. This method is described as useful only to separate different cell types in a whole blood sample such as red and while blood cells, doing cell counts and the like. It also describes use in separating populations of leucocyte cells into sub classifications. The patent does not disclose comparing samples of the same cell types for differences in measurement factors, other than quantity of cells information it doesn't discuss any measurement factor observations at all and does not disclose use of this technique to identify cells which have been exposed to an antigen. The patent further does not describe control methods and does not describe use in diagnosis of disease states other than inferring it can perform cell counts.

The apparatus for scanning a fluid sample (for example by fluorescence analysis using computer pixel modeling) is known in the art. Commercial fluorescence readers are readily available and can be programmed by one skilled in the art to read and analyze fluorescence data as needed.

It would be desirable therefore, to have both a device and methods for screening, ex vivo, whole blood or other fluids having leucocytes, for previous exposure to antigens that is easy and safe to use by the person performing the test, is both quantitative and qualitative, can be done in the lab or the field, is accurate, can be done in a relatively short period of time, uses microvolumes (a drop) of blood and wherein the device is disposable.

BRIEF SUMMARY OF THE INVENTION

It is an object of the invention to provide both an assay and microfluidic device that can be used to test leucocyte containing body fluids such as undiluted whole blood for previous exposure to a predetermined antigen that is relatively quick, easy to do, accurate, wherein the device is disposable, the method is relatively safe, can be done in the lab or the field, uses very small volumes of blood, can test for multiple measurement factors or modes or tests for multiple antigens. The above objectives and more are achieved by the present invention and are distinct novel advantages as can be further seen from the disclosure herein.

The method of the invention is a leucocyte antigen mediated microfluidic assay for testing a leucocyte containing fluid from a subject for prior exposure to a predetermined antigen which would have caused the leucocyte to become presensitized comprising:

performing a first test comprising the steps of:
  a) placing a microvolume first sample of the subjects leucocyte containing fluid in a first sample microchamber;
  b) transporting the first sample to a first reaction microchamber containing the predetermined antigen and an antigen accelerator and allowing them to react together for a predetermined time;
  c) transporting the reacted first sample to a first observation microchamber;
  d) mixing one or more leucocyte observation colorants with the reacted first sample during transportation to the observation microchamber or in the observation microchamber;
  e) optically performing a multifield scan of the reacted sample in the first observation microchamber under conditions which allow the measurement of at least one measurement factors of the leucocyte in the reacted first sample;

performing a second test comprising the steps of:
  a) placing a microvolume second sample of the subjects leucocyte containing fluid in a second sample microchamber;
  b) transporting the second sample to an antigen free second reaction microchamber containing the same antigen accelerator as the first test and allowing them to react for a predetermined time;
  c) transporting the second sample to a second observation microchamber;
  d) mixing the same leucocyte observation colorants as the first test with the reacted second sample during transport to the second observation microchamber or in the second observation microchamber;
  e) optically performing a multifield scan of the reacted second sample in the second observation microchamber under conditions that allow the measurement of the same leucocyte measurement factors measured in the first test;

comparing the results of the first test scan to the second test scan to determine if any differences between the two scans are due to a leucocyte-antigen mediated response.

The device of the invention is a microfluidic device for use in performing a leucocyte-antigen mediated microfluidic assay in a leucocyte containing fluid sample from a subject comprising:
  a) a first fluid sample addition microchamber in fluid communication by means of a first fluid channel with a first sample reaction microchamber containing a predetermined antigen and an antigen accelerator;
  b) a first sample observation microchamber in fluid communication by means of a second fluid channel with the first sample reaction microchamber;
  c) one or more leucocyte observation colorants positioned either in the second fluid channel, the first sample observation microchamber or both;
  d) a second fluid sample addition microchamber in fluid communication by means of a third fluid channel with an antigen free second sample reaction microchamber containing the same antigen accelerator as the first sample reaction chamber;
  e) a second sample observation microchamber in fluid communication by means of a fourth fluid channel with the second sample reaction microchamber;
  f) the same leucocyte observation colorants as the first test, positioned either in the fourth fluid channel, the second sample observation microchamber or both;
  g) a means for moving at least a portion of each of the fluid samples through each of their respective fluid channels into successive microchambers.

In a specific embodiment, wherein the colorant is not cytotoxic it is also part of the invention that the first reaction microchamber and the first observation microchamber are the same microchamber; and the second reaction microchamber and the second observation microchamber are the same microchamber, In yet another embodiment the first and second sample addition microchambers are the same microchamber.

The invention also relates to a kit of parts comprising both the microfluidic device of the invention as well as the apparatus which is capable of reading the microfluidic device observation microchambers and comparing the two performed tests to determine the status of antigen exposure of leucocytes in the fluid of a test subject.

DETAILED DESCRIPTION OF THE INVENTION

Figure 1:
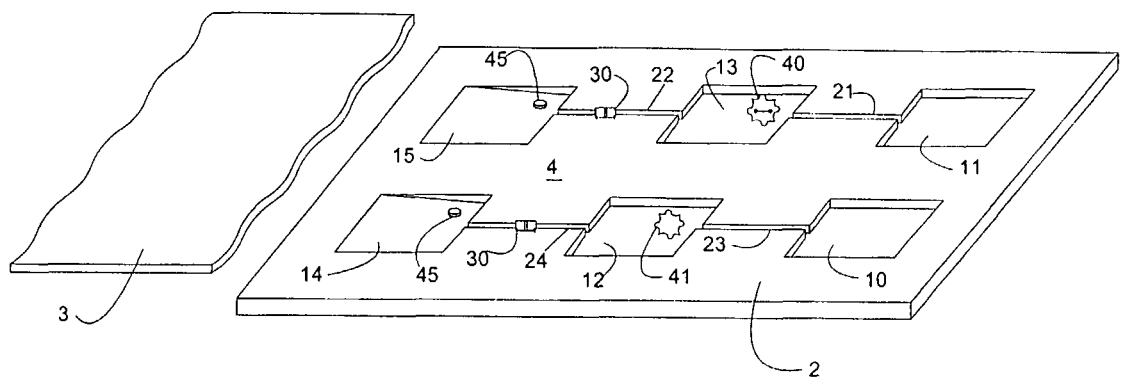
FIG. 1 shows a plan perspective view of the microfluidic device of the present invention.

The present invention relates to a microfluidic device and a leucocyte antigen mediated microfluidic assay (LAMMA) for determination if a subject has been previously exposed to a predetermined antigen by testing the subjects' leucocyte containing body fluid sample to see if the leucocytes are presensitized to the predetermined antigen. The general description of both the device and method are stated in the Brief Summary above. This detailed description defines the meaning of the terms used herein and specifically describes embodiments in order for those skilled in the art to practice the invention. The LAMMA and microfluidic device in general comprise two simultaneous tests on a microfluidic device that can be in one embodiment, disposable. One test is done exposing leucocyte containing body fluid such as whole blood or other leucocyte containing body fluid such as milk, lymph fluid, spinal fluid or the like, to a predetermined antigen while the other test is a control which essentially contains the exact same test as the first test minus the predetermined antigen. The tests are compared for difference in leucocyte measurement factors and those differences determine if the subject has been previously exposed to the predetermined antigen i.e. if the leucocyte is presensitized. A distinct advantage of the method of the invention is that it is not only qualitative in nature, it is quantitative in nature and therefore leucocyte response, which is a direct indicator of level a vaccination protection, can be determined by such measurements using the present invention. Vaccination response can be used after initial vaccination to determine if titer levels are sufficient for protection or after an extended period of time to determine if a previous vaccination is still providing sufficient levels of protection. This can be accomplished by observing the number of reacting cells that exhibit a measurement factor, as well as the plus or minus intensity of the difference between the 2 tests.

By "subject" is meant herein to be any animal especially birds, mammals and especially humans, that have whole blood circulating leucocytes or other body fluids containing leucocyte, especially T-lymphocytes, and especially memory T-lymphocytes that produce a measurement factor change after exposure to an antigen. The antigen exposure of the subject is either from an environmental source such as infection or disease caught from another animal or the environment, vector transmitted antigens, zoonotic transmitted antigens or in the case of bio-terrorism an antigen introduced to the subject population by artificial means such as disposal in water sources, release into the environment, insertion into the food supply, use of mail systems or other mechanical means and the like.

By "leucocyte" and "presensitized leucocyte" is meant any of the sub categories of leucocytes that have been exposed previously to an antigen or would participate in reaction to re-exposure to that antigen that will then exhibit a one or more measurement factors upon a subsequent exposure to the same antigen. While previous assays have limited testing to a particular leucocyte subclass such as T lymphocytes it is now possible to measure changes in all leucocyte that exhibit a measurement factor regardless if it is directly or indirectly reacting with an antigen. Cells include not only all lymphocytes but neutrophils and other white blood cells. A distinct advantage of this assay occurs when assaying for neutrophil measurement factors in that they are much more plentiful than other leucocytes and therefore smaller samples and less search time and effort is required to find them in a sample.

Whole blood or other body fluids used in the test can be used essentially undiluted, although, if desired, some degree of dilution could occur but is not necessary for the practice of this invention. Because in the practice of this invention fluids will be exposed to air, when the fluid is whole blood, the possibility of coagulation exists and suitable anticoagulants should be introduced to insure the blood remains fluid. Anticoagulated whole blood as claimed herein can be produced by adding anticoagulants to whole blood either prior to the addition of whole blood to the sample microchamber or anticoagulant can be added to the sample microchamber either before or after addition of the blood to the microchamber.

The LAMMA and microfluidic device of the present invention requires only microvolumes of body fluid. In general, those amounts would be in microliter amounts and in general about 100 microliters or less, about a single drop of blood or other body fluid, for each microchamber. In the case where a single microchamber is used as the first and second sample microchamber, it is possible to start with a single drop of body fluid. Single drops of body fluid range from about 10 microliters to about 60 microliters. Whole blood and other fluids can be taken from either a previous larger sample or taken directly from the subject for the method of the invention, for example, a drop of blood obtained by lancet. Placement can then be made into the microchamber by either direct placement from the lanced body part or by mechanical means such as by dropper or pipette.

By "fluid communication" between microchambers means that channels are produced of appropriate size for the microvolumes of leucocyte containing body fluid being tested. Small capillary type channels in the device having a diameter of about 30 micrometers to about 2 millimeters, more or less are appropriate. Where a fluid contains larger molecules than in whole blood, for example the large proteins in milk, appropriate larger channels can be used. In order to move the fluid between chambers a means for moving the fluid must be used. One particular method of moving body fluids between microchambers is capillary action that will move fluid almost immediately between microchambers. Where slightly larger channels are used between microchambers a micropump of appropriate size can be used. One skilled in the art would be able to determine other appropriate means for further moving fluids between microchambers. Where it is desirable to stop the flow of fluid between microchambers in the microfluidic device for any period of time such as when it arrives in the reaction microchamber for the reaction time, a small valve or other blocking device can be inserted in the following channel to prevent capillary action or other transportation means from occurring prior to the end of the reaction time.

The "sample microchamber" of the invention is designed to accept the whole blood or other leucocyte containing body fluid sample of the subject. It can be two separate microchambers, one for each of the two tests performed by the method or it can be a single microchamber with dual fluid communication means such as channels, one for each test provided, such that roughly equal portions of the fluid sample are delivered for each of the two reaction microchambers. The microchambers are design to accept the microvolumes of fluid from the subject, so therefore their volume is roughly equal to or slightly larger than the anticipated test sample of body fluid.

The "reaction microchamber" is in direct fluid communication with the sample microchamber. It is designed to accommodate the fluid sample in size similar to the sample microchamber but also will have space for additional reaction components. In the case of the first test of the present invention, the reaction microchamber contains the predetermined antigen or a plurality of predetermined antigens and an antigen accelerator. In the case of the second test of the invention, it only contains the antigen accelerator and is antigen free.

The "predetermined antigen" as used herein is an antigen that the fluid sample is to be tested in order to determine if the subject providing the sample has had a previous exposure to the antigen. Any antigen that produces a leucocyte measurement factor can be such predetermined antigen and selected by the tester who wishes to test the subject for exposure to the predetermined antigen. Bioterrorist type antigens for anthrax, botulism, the plague, smallpox, tularemia, hemorrhagic fever, brucellosis, glanders, melioidosis, psittacisis, Q fever, typhus, encephalitis, toxins, afflatoxins, nipah, hantavirus, west Nile fever, hendra and rift valley fever are notable test antigens of high consequence. Other disease states and antigens of lower consequence including but not limited to, tetanus, diphtheria, and monslia, chemicals known to activate leucocytes, tuberculosis, and the like may also be tested. In the case of non-human mammals African horse sickness, African swine fever, akabane virus, avian influenza, bluetongue, bovine spongiform, swine fever, coccidioidomycosis, bovine pleuropneumonia, caprine pleuropneumonia, foot and mouth disease, goat and sheep pox, heartwater lumpy skin disease, catarrhal fever, menangle virus, Newcastle disease, peste des petits ruminants, rinderpest, screwworm myiasis, swine vesicular disease, vesicular stomatitis, and the like can be tested. It is clear that a subject can be exposed to either a low consequence antigen, that is one who's result to the subject is either low impact or recoverable or exposed to high consequence antigens such as bioterrorist agents that result in serious injury or death. Another source of antigens are those antigens purposely introduced into a subject by way of vaccination and the determination of the efficacy of the vaccination is desired, e.g. vaccines against the flu, vaccines against bio-terror agents or vaccines against cancer antigens.

A sample of the antigen proportional to the microvolume of body fluid is placed in the first reaction microchamber. It can be as a liquid or in a dry powder or coating of the microchamber or by other method known for placing materials in micro type chambers.

The "antigen accelerator" is also placed in the first reaction microchamber as well as the control second reaction microchamber. The antigen accelerator is a composition which stimulates, amplifies and or accelerates the production of measurement factors in leucocyte upon exposure to an antigen. These compositions are known in the art and are being further developed. For example, $\alpha_2$-macroglobulin is known as an antigen accelerator (Vaccine 2001, 20, 554-562). The antigen accelerator is placed in the reaction microchambers as a liquid or powder or coating similarly to the antigen. Where the antigen accelerator needs to be in contact with the antigen as is the case with most known accelerators, the antigen accelerator can coat the predetermined antigen or antigens and the resulting mixture used in the reaction chamber.

Upon entering the first reaction microchamber the fluid sample will begin reacting with the combination of antigen(s) and antigen accelerator. The "reaction time" of the invention will be the time the leucocyte in the fluid need in the presence of the antigen and accelerator to develop measurement factors. The presences of the antigen accelerator is designed to produce, in such microvolumes, very quick reactions times. In other words, the measurement factors would develop an antigen reaction optimally in about an hour or two. The exact time will vary plus or minus depending on the predetermined antigen but one skilled in the art can determine that exact time for the predetermined antigen in the presence of the antigen accelerator. In the case of multiple predetermined antigens being added to the reaction microchamber, the predetermined time would be the longest predetermined time of each of the predetermined antigen reaction times separately.

After the predetermined time the first sample is caused to be transported to the observation microchamber. In one embodiment of the invention the reaction microchambers and observation microchambers can be the same microchambers when one is not using a colorant that is cytotoxic. Transportation is previously described and can be accomplished simply by opening a valve between the reaction and observation microchambers and allowing capillary action to move the liquid. It is necessary during this process to mix the reacted fluid with one or more leucocyte observation colorant. The leucocyte observation colorant can be placed in the channel between microchambers or can be placed in the observation microchamber itself or both. This can be done by dry coating either the channel or microchamber.

"Leucocyte observation colorants" are compounds known to differentially color morphological factors, in a leucocyte and cause various colorations (spectral factors) at various wavelengths based on the leucocytes reaction or lack of reaction to the antigen. Examples of such colorants include but are not limited to: Astrozone Orange, Also known as Basic Orange 21 which is 3-trimethyl-2(2-(2-methyl-1H-indol-3yl)-vinyl)-3H-indolium chloride. Other possible colorants include Acridine Orange, Ethidium Bromide, Griefswalder's Blue, Blue Borrel, Rhodanile Blue, Toluidine Blue, Night Blue, Prune Pure, Hofmann's Violet, Basic Red 13, Basic Violet 16, Carbocyanine K-5, and mixtures of above. Many of the colorants are cytotoxic. When selecting a cytotoxic colorant it is preferable to allow it to be in contact with cells the minimum time. In the embodiment of the invention where the observation and reaction chambers are separate the minimum time in contact is achieved. Where the predetermined time is short enough or the colorant is not cytotoxic the embodiment where the reaction and observation microchambers of each test are the same microchamber can be used.

The "observation microchamber" is a chamber for which leucocytes measurement factors can easily be observed by optical scan. The microchamber is designed to spread out the fluid sample in such a manner to make a field by field, YYZ scan possible. See, for example, U.S. Pat. No. 6,350,613 which describes such microchamber and optical scan thereby. In embodiments described herein the observation microchamber can also be the reaction microchamber.

Upon entry into the observation microchamber the fluid can be optically scanned for leucocyte measurement factors based on color produced by various morphological and spectral factors by the leucocyte observation colorant. This is done in one embodiment using multi-wavelength fluorescence image analysis as described in U.S. Pat. No. 6,350,613. Therein a method is described for differentiating different cells or cell subtypes by observation of the fluorescing cell at two or more wavelengths. One could also use an optical microscope or any other manual or automatic method or device for observing fluorescence i.e. observing or scanning the samples. It has been discovered by the inventors hereof, that in addition to cell subtypes, measurement factors of leucocytes can be determined using the described method of the present invention. Morphological factor changes can easily be determined by the scan picking up the different physical characteristics highlighted by the colorant and noting that they represent normal leucocyte or antigen reacted leucocyte. In addition to morphological factors, spectral factor differences can be measured, the differences between normal and antigen reacted leucocytes can also be compared.

Fluorescence image analysis is now widely carried out and cell based machines and hand microscopes as well as ones that digitize and analyze information are readily available. Companies such as Universal imaging, for example, make machines that can easily be adapted by one skilled in the art for use with the method and device of the invention. In the alternative, these machines could easily be modified to accept the device of the invention and automatically perform the desired scan. Image analysis software is in general use and can be used to create digital pixels of the image viewed by the scan and assign intensity and color numbers for each pixel. The digital data can then be used in not only finding morphological factors it can be used in a number of ways to determine spectral factors.

Measurement factors include both morphological factors and spectral factors. Morphological factors include shape, diameter, area, volume and perimeter of the cell, area and volume of nucleus, shape of nucleus, percentage of total volume occupied by nucleus, eccentricity of nucleus, etc. Spectral factors include sum of all the pixel intensities that make up the total cell area at any of 16 different emission wavelengths, ratios of each sum to any other sum, average pixel intensity at each of emission wavelength, coefficient of variation of the pixel intensities at each of 16 wavelengths, sum of the total pixels in the area identified as cytoplasm (not nucleus), ratios of each sum to any other sum in the cytoplasm, average pixel intensity at each wavelength of cytoplasm pixels, coefficient of variation of the cytoplasm pixels at each of 16 wavelengths, geometric center of light emitted by all pixels, etc In general at least 3 measurement factors should be compared to prevent false positives and 5, 10, 15 or more factors can be compared easily using computer analysis of the resulting scan. Measurement factors can also be quantified using measured morphological and spectral factors measured by multi-wave fluorescence image analysis and measuring the number or intensity of reacted leucocytes exhibiting the measurement factors as compared to the control test of the invention.

Image analysis of multi-wave fluorescence information converts picture information into a series of digital information as pixels of differing color and intensity. This information may be stored and compared in a computer, pixel by pixel. By comparing the control test scan to the antigen scan and comparing the change of both color and relative intensity gives the process of the invention in addition to the qualitative information, determining if the leucocyte is responding to the antigen, it gives a quantitative result by the number and intensity of pixels corresponding to the intensity of the antigen response of the responding leucocyte. The greater the number and intensity of pixels, the greater the response and therefore the greater the production of presensitized leucocyte for the given antigen. One skilled in the art can measure the measurement factors using the color variations and/or other calorimetric measuring factors known in the art as well as the image analysis by multi-wavelength fluorescence. By looking for leucocyte changes based on cell-mediated immune response rather than antibody production the method of the invention is able to quickly and accurately provide the objects of the invention.

The second test of the invention is identical to the first test except the second reaction microchamber is antigen free. In other words, as a control, all the factors of the second test are identical except for exposure to the antigen. This includes the predetermined time, fluid sample, colorant and the like. By running the same test on the second sample the digital data may be compared to the first test data. By comparing the differences between the two tests it can be seen statistically and visually when there is a difference in measurement factors of the leucocyte sample of the patient. These differences are an indicator of a positive preexposure to the predetermined antigen.

In one embodiment of the invention the device is made in a disposable format. This device would be made of plastic or other inexpensive disposable material. The device of the invention containing the subject sample can be discarded in an appropriate manner and the tester need never come in contact with the contents. The disposable microfluidic device can be constructed credit card size more or less similar to other microfluidic assays such that it fits in a reader portion of an image analyzer that can read the calorimetric data from the tests by either moving the test device around or moving a reader in the analyzer or both to take readings of the type in the above referenced patents and also described herein.

Mode Of Operation

Referring now to the figures, FIG. 1 is a plan view of the microfluidic device of the invention where the reaction chambers and observation chambers are separate. The leucocyte-antigen assay microfluidic device 2 has a length and width similar to other standard disposable microfluidic assay tests of its type. So a 2 in by 4 inch size or other size as needed to fit the analyzer being used and fit the microchambers as described herein is used. As shown in this embodiment the microfluidic device 2 is rectilinear however any convenient shape can be employed that would allow the tests to be placed thereon. The device 2 is fitted with a sealed cover 3 which covers the entire top of the device 2 except for the sample microchambers 10 and 11 that remain uncovered to allow a sample of fluid to be placed therein. The size of the microchambers is as described elsewhere herein but in general allows for a drop or two of fluid from a test subject. In this embodiment sample microchamber 11 is for the first test and sample microchamber 10 is for the second test (i.e. the control test). The shape of these microchambers is not critical but should be a size that accommodates the means being used to add the fluid sample whether by dropper or dropped from a lanceted finger or the like.

Fluid channels 23 and 21 flow from their respective sample microchambers 10 and 11 and deliver the fluid sample to reaction microchambers 12 and 13 respectively. These reaction microchambers 12 and 13 are roughly the same size as the sample microchambers. Since in this embodiment capillary action will be moving the sample it is anticipated that some fluid will remain in each of the microchambers shown as well as the channels. The reaction chamber 13 is coated with both a predetermined antigen/antigen accelerator complex 40, that in this embodiment coats the bottom of reaction chamber 13. Reaction chamber 12 is coated with only the antigen accelerator 41. Fluid channels 22 and 24 deliver the fluid sample to observation microchambers 15 and 14 respectively. Interposed in each of channels 22 and 24 are microvalves 30. Each microvalve 30 can block the capillary flow from a reaction chamber to prevent flow into the observation chambers 14 and 15 until the predetermined time described above has elapsed. Observation microchambers 14 and 15 have a different geometry than the other 4 microchambers in this embodiment. Observation microchambers 14 and 15 have a wedge shape tapering from a widest point where the fluid channels 22 and 24 enter the microchambers to the far end of the observation microchambers 14 and 15 where the thickness is roughly the thickness of a single blood cell or about 3 microns. Disposed in fluid channels 22 and 24 are leucocyte observation colorants 45.

Figure 2:
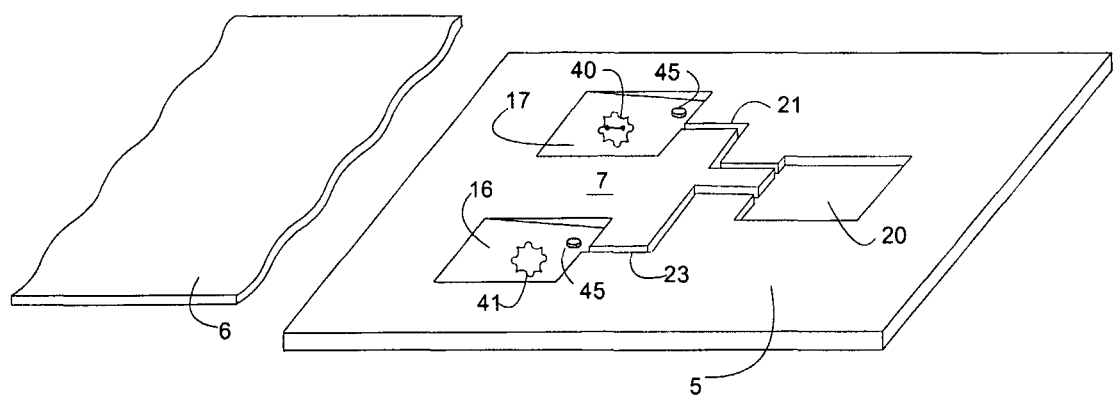
FIG. 2 shows a plan perspective view of the microfluidic device of the present invention wherein the reaction chambers are also the observation chambers and the first and second sample microchambers are the same microchamber.

Now referring to FIG. 2. FIG. 2 to is a plan perspective wherein the first and second sample microchambers are the same microchamber and wherein each of the respective first reaction microchamber and first observation microchamber; and second reaction microchamber and second observation microchamber are the same. This embodiment of the invention is useful where the colorant is not cytotoxic or where the predetermined time is so short as to not cause cytotoxic problems. Referring to the drawing, microfluidic device 5 can be fitted with cover 6 which covers the entire top 7 of device 5 except for the opening for sample chamber 20. The joint first and second sample microchamber 20 is the chamber for adding the body fluid sample to be assayed. Two fluid channels 21 and 22 for the first and second test respectively are in fluid communication with sample chamber 20. They are also in fluid communication with joint reaction/observation microchambers 17 (for antigen) and 16 (for control). Each of microchambers 17 and 16 are wedge shaped similar to the observation chambers 14 and 15 of FIG. 1. Herein however microchamber 17 contains the antigen-antigen accelerator complex as well as the leucocyte observation colorant 45.

EXAMPLE

Latent Johne's Disease infection in dairy cattle. Johnes is the second costliest disease in the dairy industry and it is caused by the *Mycobacterium avium* paratuberculosis organism (MAP). The organism is known to be one of the slowest growers in the tuberculosis family, is extremely difficult to detect in latent asymptomatic infections, and it generates practically no antibody response in dairy cattle for months, or even years. However, upon initial exposure to cattle, MAP triggers an initial response in a subpopulation of bovine leukocytes (memory T-cells). The record of that initial encounter is retained in the immunological memory of the T Cell.

A bovine whole blood sample that been previously exposed to MAP is placed in the sample microchamber of the microfluidic device of the invention. The blood is then moved to the first reaction microchamber and re-stimulated using protein antigens that are unique to MAP, in combination with the antigen accelerator $\alpha_2$-macroglobulin. After the stimulation with these proteins for one to two hours, the sample is moved to the observation microchamber and the sample is treated with the colorant, Astrozone Orange which had previously been placed in the observation microchamber. A second test is run with the blood identical to the first with the only difference being the absence of antigen in the reaction microchamber. The level of T cell response is quantified scanning the cells in the observation microchamber of both the first and second test and counting the number of T Cells that show a response to the presence of the unique antigen as evidenced by a marked change in the morphological and spectral factors in the first test as compared to the cells in the second test that does not contain the MAP antigens.

Since changes and variations of embodiments and modes of the invention may be made without significant departure from the concept and scope of the invention, such embodiments are not intended to limit the invention. Rather they are intended to indicate the broad teaching and substitutions possible within the understanding of the following claims.

What is claimed is:

1. A leucocyte antigen mediated microfluidic assay method for testing a leucocyte-containing body fluid from a subject for prior exposure to a predetermined antigen which would have caused leucocytes to become presensitized to the antigen comprising:

performing a first test comprising the steps of:
a) placing a microvolume of a first sample of the subject's leucocyte-containing body fluid in a first sample microchamber;
b) transporting, by capillary action or by use of a micropump, the first sample body fluid to a first reaction microchamber containing the predetermined antigen and $\alpha_2$-macroglobulin and allowing reaction for a predetermined time;
c) transporting, by capillary action or by use of a micropump, the reacted first sample body fluid to a first observation microchamber;
d) mixing one or more leucocyte observation colorants with the reacted first sample body fluid, wherein mixing occurs either during transport to the observation microchamber or in the observation microchamber;
e) optically performing an optical scan of the reacted first sample body fluid in the first observation microchamber to find the leucocytes in the reacted first sample body fluid; and measuring one or more measurement factors of the leucocytes;

performing a second test comprising the steps of:
a) placing a microvolume of a second sample of the subject's leucocyte-containing body fluid in a second sample microchamber;
b) transporting, by capillary action or by use of a micropump, the second sample body fluid to an antigen-free second reaction microchamber containing $\alpha_2$-macroglobulin but not containing the antigen and allowing reaction for the predetermined time;
c) transporting, by capillary action or by use of a micropump, the second sample body fluid to a second observation microchamber;
d) mixing the same leucocyte observation colorants as the first test with the reacted second sample body fluid, wherein mixing occurs either during transport to the second observation microchamber or in the second observation microchamber;
e) optically performing an optical scan of the reacted second sample body fluid in the second observation microchamber to find the leucocytes in the reacted second sample body fluid; and measuring the same leucocyte measurement factor measured in the first test;

determining whether leucocytes have reacted with the antigen by comparing the results of the first optical scan to the second optical scan, wherein any differences between the two scans are indicative of reaction of leucocytes with the antigen due to the leucocytes having been presensitized to the antigen via prior exposure.

2. The assay method of claim 1 wherein the leucocytes are T lymphocytes or neutrophils.

3. The assay method of claim 2, wherein the T lymphocytes are memory T lymphocytes.

4. The assay method of claim 1 wherein the optical scans are accomplished by multi-wavelength fluorescence image analysis.

5. The assay method of claim 1 wherein the entire method is performed on a single disposable device.

6. The assay method of claim 1 wherein the measurement factors that are measured are morphological factors, spectral factors or both.

7. The assay method of claim 1 wherein a plurality of predetermined antigens are placed in the first reaction microchamber.

8. The assay method of claim 1 wherein the reaction of leucocytes with the antigen is determined by either measuring the number, relative intensity or both of the subject's reactive leucocytes while comparing the results of the first optical scan to the second.

9. The assay method of claim 1 wherein the body fluid is whole blood.

10. The assay method of claim 9, wherein: the leucocytes are T lymphocytes or neutrophils; the optical scans are accomplished by multi-wavelength fluorescence image analysis; the entire method is performed on a single disposable device;
the measurement factors that are measured are morphological factors, spectral factors or both; and
the reaction of leucocytes with the antigen is determined by either measuring the number, relative intensity or both of the subject's reactive leucocytes while comparing the results of the first optical scan to the second.

11. The assay method of claim 1, wherein: the leucocytes are T lymphocytes or neutrophils; the optical scans are accomplished by multi-wavelength fluorescence image analysis; the entire method is performed on a single disposable device;
the measurement factors that are measured are morphological factors, spectral factors or both; and
the reaction of leucocytes with the antigen is determined by either measuring the number, relative intensity or both of the subject's reactive leucocytes while comparing the results of the first optical scan to the second.

12. A leucocyte antigen mediated microfluidic assay method for testing a leucocyte-containing body fluid from a subject for prior exposure to a predetermined antigen which would have caused leucocytes to become presensitized to the antigen comprising performing a first test comprising the steps of:
a) placing a microvolume of a first sample of the subject's leucocyte-containing body fluid in a first sample microchamber;
b) transporting, by capillary action or by use of a micropump, the first sample body fluid to a first reaction microchamber containing the predetermined antigen and $\alpha_2$-macroglobulin and allowing reaction for a predetermined time;
c) mixing one or more leucocyte observation colorants with the reacted first sample body fluid;
d) optically performing an optical scan of the reacted first sample body fluid in the first reaction microchamber to find the leucocytes in the reacted first sample body fluid; and measuring one or more measurement factors of the leucocytes;

performing a second test comprising the steps of:
a) placing a microvolume of a second sample of the subject's leucocyte containing body fluid in a second sample microchamber;
b) transporting, by capillary action or by use of a micropump, the second sample body fluid to an antigen-free second reaction microchamber containing $\alpha_2$-macroglobulin but not containing the antigen and allowing reaction for the predetermined time;
c) mixing the same leucocyte observation colorants as the first test with the reacted second sample body fluid;
d) optically performing an optical scan of the reacted second sample body fluid in the second reaction microchamber to find the leucocytes in the reacted second sample body fluid; and measuring the same at least one leucocyte measurement factor measured in the first test; and determining whether leucocytes have reacted with the antigen by comparing the results of the first optical scan to the second optical scan, wherein any differences between the two scans are indicative of reaction of leucocytes with the antigen due to the leucocytes having been presensitized to the antigen via prior exposure.

13. The assay method of claim 12 wherein the body fluid is whole blood.

14. The assay method of claim 13, wherein: the leucocytes are T lymphocytes or neutrophils;
the optical scans are accomplished by multi-wavelength fluorescence image analysis; the entire method is performed on a single disposable device; the measurement factors that are measured are morphological factors, spectral factors or both; and
the reaction of leucocytes with the antigen is determined by either measuring the number, relative intensity or both of the subject's reactive leucocytes while comparing the results of the first optical scan to the second.

15. The assay method of claim 12, wherein: the leucocytes are T lymphocytes or neutrophils; the optical scans are accomplished by multi-wavelength fluorescence image analysis; the entire method is performed on a single disposable device;
the measurement factors that are measured are morphological factors, spectral factors or both; and
the reaction of leucocytes with the antigen is determined by either measuring the number, relative intensity or both of the subject's reactive leucocytes while comparing the results of the first optical scan to the second.

* * * * *